United States Patent [19]

Mosimann et al.

[11] Patent Number: 4,507,085
[45] Date of Patent: Mar. 26, 1985

[54] DENTAL INSTRUMENT WITH HANDPIECE

[75] Inventors: David Mosimann, Bienne; Theodor Walther, Lengnau b. Biel; Jean-Pierre Schnider, Bienne, all of Switzerland

[73] Assignee: Bien-Air, Switzerland

[21] Appl. No.: 569,941

[22] PCT Filed: Feb. 18, 1981

[86] PCT No.: PCT/CH81/00019
§ 371 Date: Oct. 19, 1981
§ 102(e) Date: Oct. 19, 1981

[87] PCT Pub. No.: WO81/02249
PCT Pub. Date: Aug. 20, 1981

Related U.S. Application Data

[63] Continuation of Ser. No. 314,063, Oct. 19, 1981.

[30] Foreign Application Priority Data

Feb. 18, 1980 [EP] European Pat. Off. ........ 80810060.6

[51] Int. Cl.³ ................................................ A61C 1/08
[52] U.S. Cl. ...................................... 433/126; 433/131
[58] Field of Search ................................. 433/126, 131

[56] References Cited

U.S. PATENT DOCUMENTS 4,020,556  5/1977  Sotman .................................. 433/29
4,080,737  3/1978  Fleer .................................... 433/126
4,182,038  1/1980  Fleer .................................... 433/126

FOREIGN PATENT DOCUMENTS 1014334  6/1962  United Kingdom ............... 433/126

Primary Examiner—Robert Peshock
Attorney, Agent, or Firm—Parkhurst & Oliff

[57] ABSTRACT

The dental instrument with handpiece comprises an intermediate section (4) containing a micromotor. A handpiece (1) with a head (2) carrying a tool (3) is plugged in the front end of the intermediate section (4) so as to form a unit block therewith. At the back end thereof, the intermediate section (4) carries an adaptor comprising a part (10) integral with said section (4), and a part (9) which may rotate freely in the part (10) about the instrument axis. Said part (9) receives the adapter (8) integral therewith, of a flexible sheath (7) which connects the instrument to a supply station and brings thereto, besides the power and driving flux for the micromotor, air and water for a jet (15) of fine water droplets in the direction of the work location, as well as a lighting through an optical fiber thereof, through conduits (6,11,12,13,21) contained in the sheath (7) and going through the adaptor (9,10) separately.

16 Claims, 6 Drawing Figures

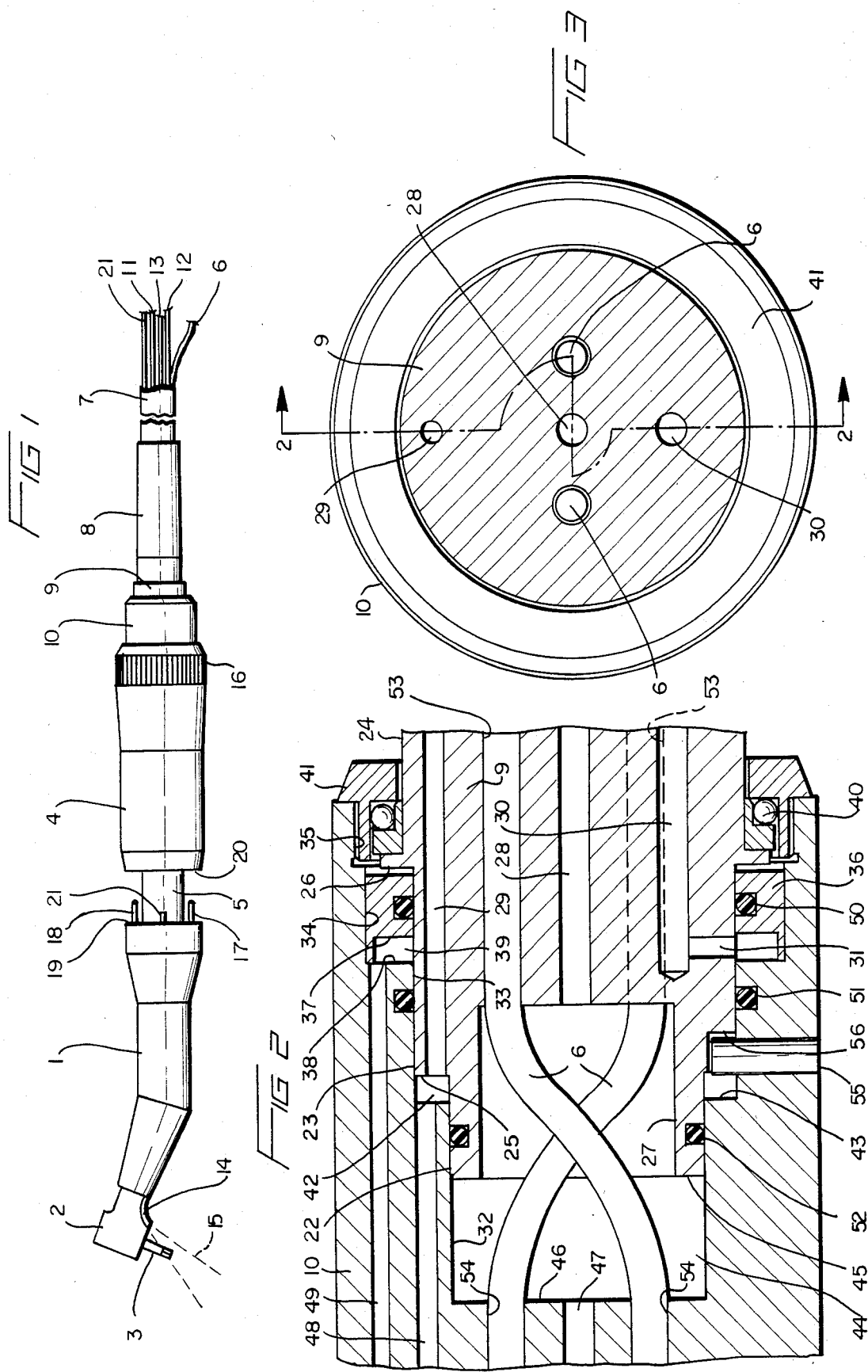

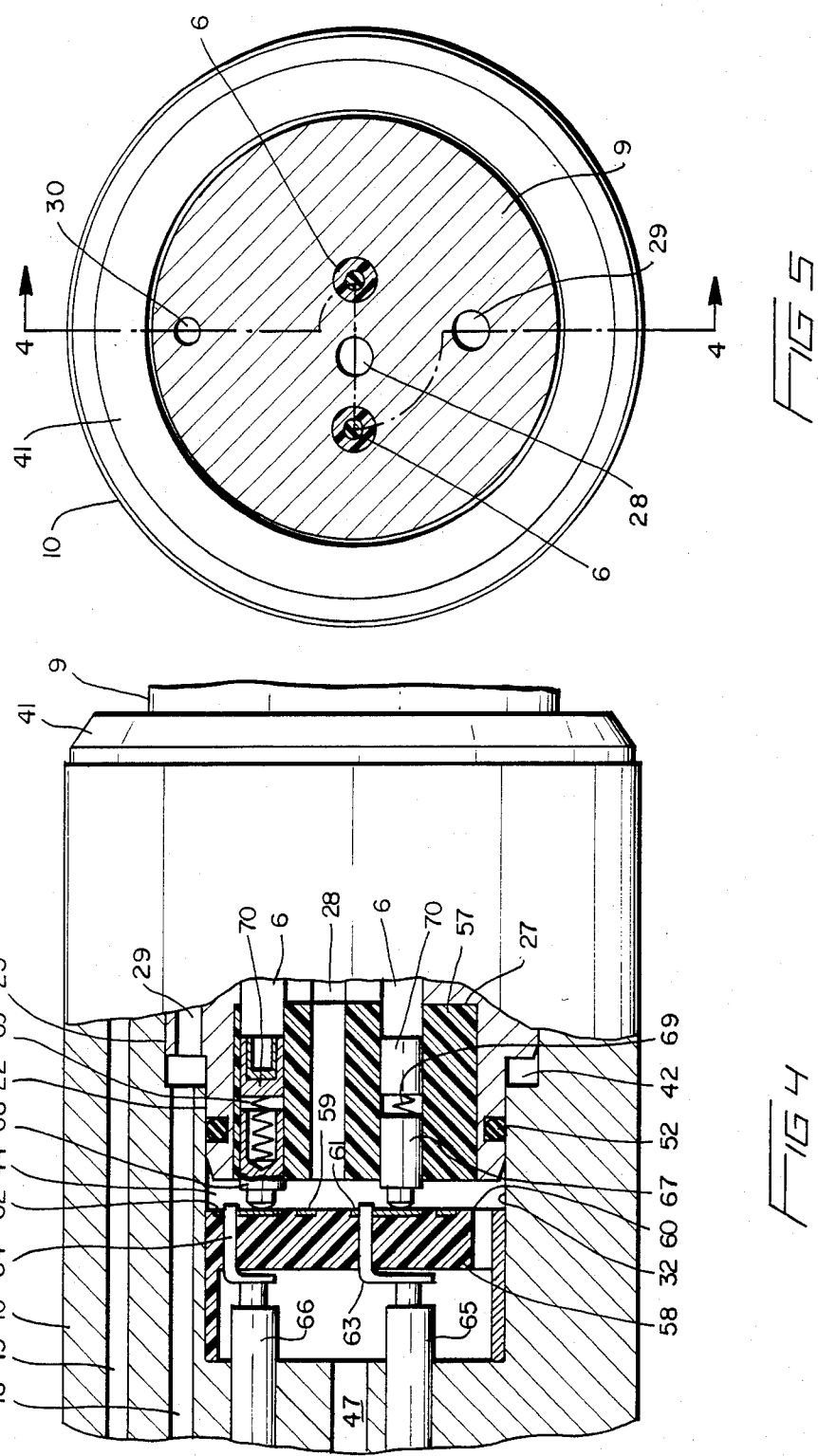

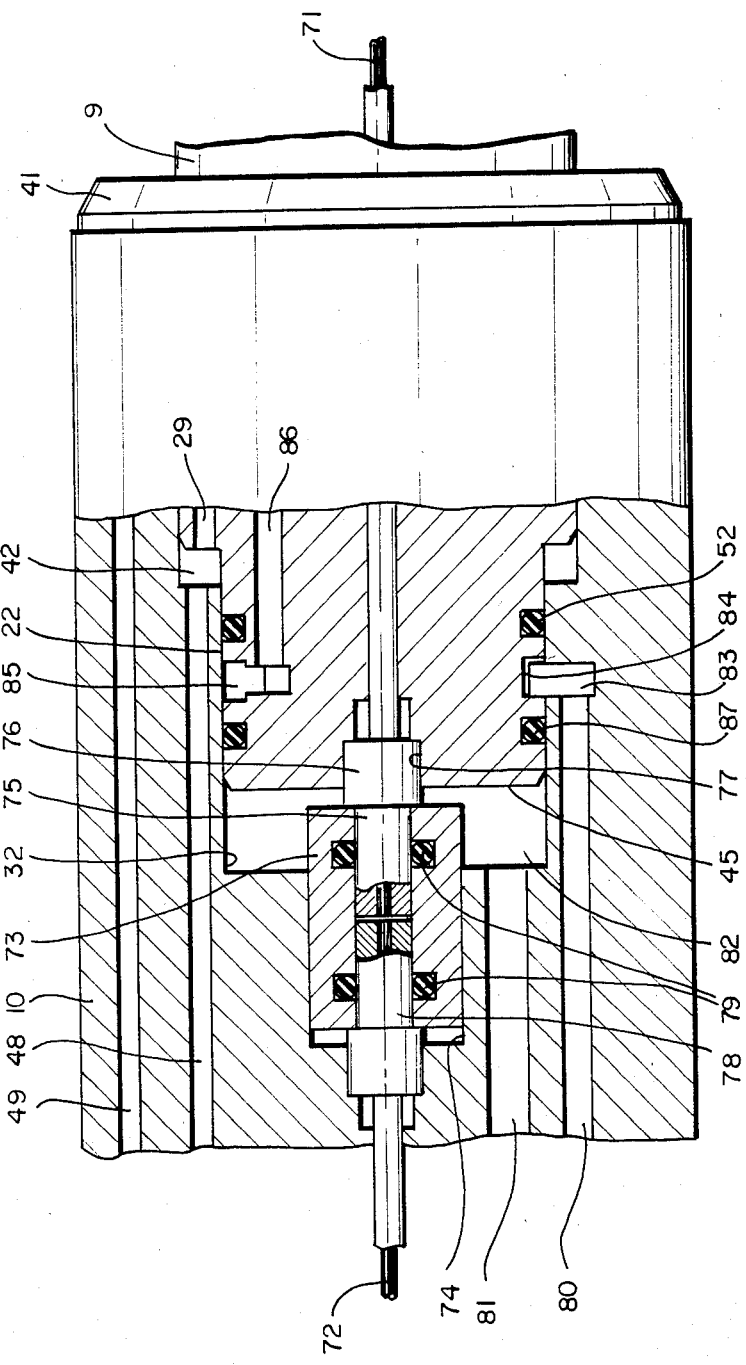

DENTAL INSTRUMENT WITH HANDPIECE

This is a continuation of application Serial No. 314,063 filed October 19, 1981.

This invention relates to dental instruments including a handpiece comprising a tool carrying head being removably mounted at the fore end of an intermediate section of the instrument, which contains a micromotor for driving the tool carried by the head of the handpiece, the rear end of the intermediate section being connected to a supply source by means of a flexible sheath and the handpiece being freely rotatable relative to said sheath, around the axis of the instrument.

With the instruments of this type which are known, it is the handpiece alone which is rotatable. The intermediate section containing the motor for its part is rigidly connected to a tip means secured to the end of the flexible sheath connecting the dental instrument to the supply source. To ensure the rotational motion of the handpiece, its rear end is provided with a bore fitted on a central sleeve of the intermediate section, which protrudes from its fore end and through which pass members connecting the rotor of the micromotor to the tool borne by the head of the handpiece. Since the micromotor rotates at relatively high speeds with modern dental instruments, it is important that the working place of the tool is cooled while blowing off the debris produced by that tool. For this purpose, the handpiece is provided either with a single nozzle arranged for spraying the working place with an air and water mixture, or with a pair of nozzles placed side by side to blow toward the working place of the tool, the one, water, and the other one air atomizing said water. These fluids are supplied by the supply source. They are fed to the instrument by tubes located in the flexible sheath and they pass through the intermediate section and the handpiece by means of conduits provided entirely or at least partially inside elements.

In order to connect a conduit of the intermediate section to a conduit of the rotatable handpiece, the first solution that suggests itself consists of a flexible tube extending on the outside of the instrument between an outlet of the intermediate section and an inlet of the handpiece. It is also the first one that has been introduced in practice. In this case the flexible tube usually forms part of the handpiece to which it is permanently connected and at its free end it carries a plug-in tip means which can be inserted in the intermediate section.

Because of the bulk of such a flexible tube, the handpiece comprises a single nozzle. An air and water mixer is provided upstream of said flexible tube possibly in the tip means of its free end, so that a single external tube suffices to produce the cleansing and cooling jet (CH-PS No. 604 670).

That known solution has, however, the drawback that the rotary motion of the handpiece is limited by the length of the outside tube. Moreover, the longer the tube, the greater the risk to be torn away upon geting caught on some foreign body member. It can also interfere with the handling of the instrument because it precisely extends in the area thereof which is held between the finger tips.

Therefore, solutions with air and water conduits entirely enclosed within the instrument parts are preferred today. The connection between a conduit of the intermediate section and the corresponding conduit of the rotatable handpiece is then ensured by an annular space provided between two adjoining surfaces of the intermediate section and of the handpiece, the hermeticity of that annular space being ensured by means of two packings arranged on both sides thereof, in grooves either of the intermediate section or of the handpiece. In practice, these grooves are formed in cylindrical surfaces and not in plane surfaces, in order that the packings do not drop out of their lodging when the handpiece is changed (GB-PS No. 1 519 513, DE-PS No. 2 334 448, CH-PS No. 604 670).

On attaching a handpiece to the intermediate section of the instrument, as is frequently done, said packings are thus either compressed to enter a bore or stretched to engage a cylindrical surface, depending on whether they are located in grooves of a cylindrical bearing surface or in grooves of a bore. In both instances it is the fore rim either of a bore or of a cylindrical bearing which produces that deformation of the packings. Now, often enough it occurs that the packings are damaged by that edge upon too hasty and somewhat clumsy hook-up of the handpiece to the intermediate section.

The solution provided by the present invention avoids that risk. The connection of the conduits of the intermediate section to those of the handpiece is direct. It may be carried out merely by introducing the protruding inlets of the handpiece conduits into the corresponding outlets of the conduits of the intermediate section, for instance, in the manner used in every household of inserting an electrical plug into a socket.

The rotary adapter of the instrument according to the present invention, which is provided at the rear end thereof, has also the advantage to form a unit which the dentist need not disassemble. The actual adapter is assembled once and for all and then handled as a single piece. A possible disassembling of that rotary adapter occurs, indeed, only for a repair or a retrofit, these operations being carried out by specialized mechanics and not by the dentists.

With respect to known instruments, the handpiece of which turns relative to the intermediate section containing the micromotor, the instrument according to the invention has moreover the advantage of improving the operating conditions. The tool orientation can be modified by promation or by supination, i.e. by a rotation of the whole hand and the forearm, without having to modify the position of the finger tips on the handpiece, as it has to be done with the known instruments, in order to cause the handpiece to turn with respect to the intermediate section. With the instrument according to the invention, the manual sensitivity thus strictly remains unchanged whatever orientation the tool may be given in the mouth of the patient.

The idea of facilitating the manipulation of a dental instrument in that way is not new per se. It has been embodied in most of the handpieces, the head of which is fitted up with an air turbine, to the rotor of which the tool to be used is secured in order to be driven at very high speed: several hundreds of thousands r.p.m. (U.S.-Pat No. 3,521,359, FR-PS No. 2 173 034, FR-PS No. 2 199 964, U.S.-Pat. No. 3,921,296, U.S.-Pat. No. 4,177,564, FR-PS 2 403 065).

Instruments according to the present invention comprisng a micromotor in an instrument part which is practically within the hand of the dentist, this micromotor driving the tool by a mechanical transmission means at speeds ranging between 20,000 and 40,000 r.p.m., but with a relatively strong torque, the easy manipulation mentioned here-above was, till now, given up on, perhaps because of the expected difficulties in passing through the rotary adapter not only the air and water to cool the working place, but also the means conveying the necessary energy for actuating the micromotor through a rotary adapter.

However, providing the pivot point between the handpiece and the flexible sheath upstream and not downstream from the micromotor contained in the intermediate section of the instrument does not at all restrict the possibilities in outfitting the instrument. It appears, indeed, as defined by claim 2, that the rotary adapter provided at the rear end of the instrument can be crossed longitudinally by all the usual conduits.

The connection of the air and water conduits, which is provided between the intermediate section and the handpiece in the known instruments, can similarly be provided between the two pieces of the adapter of the instrument according to the present invention, whether the micromotor contained in the intermediate section of the instrument is an electrical motor or an air motor.

Independently of the nature of this micromotor, a fiber optics can even be passed through the instrument in order to illuminate the working place, as shown by the embodiments defined by claim 7.

BRIEF DESCRIPTION OF THE DRAWINGS

Various embodiments of an instrument according to the present invention are represented here-below and by way of example in relation to the drawings in which:

FIG. 1 is a general elevational view of one embodiment of the instrument according to the invention, the handpiece being partly separated from the intermediate section of the instrument;

FIG. 2 is a cross-section on a large scale long line II—II of FIG. 3, showing a detail of another embodiment;

FIG. 3 is an end view of the right end of FIG. 2;

FIG. 4 is a part section view along line IV—IV of FIG. 5 of the same detail as that of FIG. 2, but of another embodiment;

FIG. 5 is an end view of the right end of FIG. 4, and

FIG. 6 is a view similar to that of FIG. 4, showing a detail of a last embodiment.

DETAILED DESCRIPTION OF THE PREFERRED EMBODIMENT

The instrument represented in FIG. 1 comprises a handpiece 1 having, at its fore end, a head 2 arranged for carrying anyone of the conventional tools of the dentists, in particular a milling cutter 3, and for driving it in rotation about its axis. The handpiece 1 is intended for attachment to an intermediate section 4 of the instrument, which contains an electrical micromotor of a known type. This section 4 is provided with a sleeve 5 protruding from its fore end and through which passes the shaft of the micromotor. On attaching a handpiece 1 to section 4, sleeve 5 serves as guiding means. For this purpose, sleeve 5 enters a bore in the handpiece and centers the latter on the intermediary section 4, thereby also ensuring the correct coupling of transmission means (not shown) provided between the micromotor contained in section 4 and the milling cutter 3.

Energizing the motor is ensured by a conventional supply source (not shown) through leads 6 enclosed in a flexible sheath 7 which connects the supply source to the instrument. At its downstream end the sheath 7 carries a tip means 8 which is fixed to a first piece 9 of an adapter, (also referred to as the male portion) the second piece 10 (also referred to as the female portion) of which is itself fixed to the rear end of the intermediate section 4. Piece 9 can freely rotate in piece 10 coaxially with the instrument.

During the work in the mouth of a patient, the dentist can, owing to the rotatability of the adaptor 9, 10, modify at will the inclination of the axis of the milling cutter 3, without modifying the position of the finger tips on the handpiece 1, simply by supination or pronation of the hand and the forearm, and that, without being hampered by the torsional stiffness of sheath 7.

Since the micromotor and the milling cutter 3 rotate at speeds of some tens of thousands revolutions per minute, it is mandatory to provide for cooling not only the motor, but also the working place. For this purpose, the supply source supplies the instrument with a cooling air flow for the motor through a tube 11 enclosed in sheath 7, as well as with air and water under pressure through tubes 12 and 13 also enclosed in sheath 7. The fluids under pressure flow longitudinally through the whole instrument and reach nozzles 14 arranged side by side in head 2. Nozzles 14 are directed toward the end of the milling cutter 3. The air blown by one of nozzles 14 atomizes the water coming out of the other nozzle 14 so that a jet of very fine water droplets is directed toward the working place of the milling cutter 3. By means of a rotary ring (not shown), which could be provided upstream the rotary adpater, the flow rate of the water under pressure can be modified in a manner well known in the art and the consistency of the jet 15 adjusted at will. The water supply can even be stopped in order to blow only air toward the working place, for example to blow off the debris from the working place, for instance, which have been produced by the milling cutter 3.

The water and the air jet 15 reach the nozzles 14 through conduits extending longitudinally through the handpiece 1 and protruding therefrom at its rear end as shown by the reference numerals 17 and 18. By properly orienting handpiece 1 around sleeve 5, the protruding ends 17, 18 can be inserted into the outlets of conduits (not shown) of the intermediate section 4 and communicating with tubes 12 and 13 of sheath 7. When the rear face 19 of handpiece 1 butts against the front face 20 of section 4, a conventional latching device (not shown) holds handpiece 1 axially in place on sleeve 5.

In the embodiment of FIG. 1, the supply source also supplies the dental instrument with light through a fiber-optical light guide 21 passing through sheath 7 and extending up to head 2 to illuminate the working place.

In an instrument which would be nonrotatably connected to the flexible sheath 7, the above disclosed equipment could be arranged without any difficulty. However, it will be understood that arranging said equipment in the embodiment disclosed can only succeed if one can manage to pass all the feeding lines of sheath 7 through the two pieces of the rotary adapter 9, 10, which must be capable of freely rotating within one another.

Some embodiments of that adapter are represented in detail in the following figures of the drawing.

The embodiments of that adapter are represented in detail in the following figures of the drawing.

The embodiment represented in FIGS. 2 and 3, however, differs from that of FIG. 1 by the fact that it does not comprise means for illuminating the working place of the instrument, hence no optic fiber.

Piece 9 of the rotary adapter comprises three bearing surfaces 22, 23, 24, which are separated from each other by shoulders 25 and 26. A recess 27 is formed in the center of its front face. Finally, three passages 28, 29, 30 are axially bored into piece 9. The first one, 28, along the axis of piece 9, issues into the center of recess 27 and the second one, 29, into shoulder 25. As regards the third bore 30, it is blind, but a radially bored channel 31 connects it to the bearing 23. The tip means 8 of the flexible sheath 7 (FIG. 1) is secured to piece 9 so that tube 11 communicates with passage 28, tube 12 with passage 29 and tube 13 with passage 30.

As regards piece 10 of the rotary adapter, it comprises three bores 32, 33, 34 and a thread 35. An inner ring 36 is set with force fit into boring 34. A recess 37, lathe-turned in ring 36, constitutes, together with the shoulder 38 of piece 10 located between the bores 33 and 34 thereof, an annular space 39 in the form of a groove extending all around piece 9 and in which issues the radial hole 31 of that piece regardless of what angular position piece 9 occupies relative to piece 10.

Piece 9 is held in place in piece 10 with a small axial free play by its shoulder 26 which is held by means of thrust ball bearing surface 40 placed between the ring 36 and a nut 41 screwed all the way into thread 35. The bearing 23 of piece 9 enters bore 33 of piece 10 while leaving, however, a free space 42 between its shoulder 25 and shoulder 43 of piece 10. The bearing surface 22 of piece 9 similarly enters bore 32 of piece 10 while leaving however a free space 44 between its front face 45 and the bottom 46 of bore 32. Three passages 47, 48, 49 extend through piece 10, a first one, 47, in the center thereof, from the bottom 46 of bore 32, the second one, 48, from shoulder 43, and the last one, 49, from shoulder 38. Piece 10 is secured to the intermediate section 4 of the instrument by means of a nut 16 (FIG. 1), so that the passages 47, 48, 49 communicate with the corresponding conduits of that section.

Thanks to the annular space 39, the compressed air coming through the passage 30 at piece 9 can always flow into passage 49 of piece 10 and finally reach the corresponding nozzle 14 (FIG. 1) regardless of the relative angular position of pieces 9 and 10. Similarly, the annular space 42 enables the pressurized water to pass permanently from passage 29 of piece 9 into passage 48 of piece 10. As regards passages 28 and 47 for the cooling air to the motor, they communicate with each other through the central chamber constituted by the recess 27 and the free space 44. the hermeticity of the annular spaces 39 and 42 is ensured by means of three packings 50, 51, 52.

In this embodiment the electric leads 6 supplying the micromotor are continuous. At right angle to the rotary adapter 9, 10, they pass through bores 53 and 54 of pieces 9 and 10 and they freely extend through the central chamber 27, 44 between these two pieces. In view of that arrangement of leads 6, pieces 9, 10 can obviously not be allowed to rotate indefinitely in the same direction. In this embodiment piece 10 carries a pin 55 which projects into a groove 56 of piece 9, which extends only around a portion of its periphery.

The embodiment represented in FIGS. 4 and 5 differs from the preceding one only in the manner in which the means conveying energy to the micromotor contained in the intermediate section of the instrument pass through the rotary adapter. In this embodiment a plug 57 of insulating material is inserted in recess 27 of the front face of piece 9 and a plate 58 also of insulating material is set on the bottom of bore 32 of piece 10. On the side facing piece 9 plate 58 bears two conducting rings 59, 60 which are concentric and centered on the axis of rotation of pieces 9, 10. Rings 59, 60 are electrically connected to the micromotor through arms 61, 62 and connecting pieces 63, 64 crossing plate 58 and leads 65, 66. As regards leads 6 contained in sheath 7 (FIG. 1), they end in bores of piece 9 and of plug 57. The axes of these borings are at distances from the axis of rotation of pieces 9, 10 which are equal to the mean radii of rings 59, 60. Brushes 67, 68 guided in the bores of plug 57, are pushed against rings 59, 60 by springs 69 resting on caps 70 soldered to the ends of leads 6. Plugs 67, 68 thus operate by frictional contact with rings 59, 60 when pieces 9, 10 rotate relative to each other. In any manner, whereby they establish a permanent electrical connection between leads 6 from the supply source to the leads 65, 66 connected to the motor. With respect to the embodiment of FIGS. 2 and 3, that of FIGS. 4 and 5 accordingly had the advantage to permit unlimited rotations of pieces 9, 10 relative to each other.

The last embodiment (FIG. 6) differs from the preceding ones by the fact that the micromotor contained in the intermediate section of the instrument is a pneumatic motor. With respect to the embodiments of FIGS. 2 to 5 that of FIG. 6 is equipped with fiber-optics illumination for working place.

This fiber optics comprises two strands 71, 72. The first one, 71, comes from a light source of the supply source and the second one, 72, extends toward the head 2 of handpiece 1 (FIG. 1). Inside the rotary adapter 9, 10 the two strands of the fiber optics are arranged along the axis of rotation of the two pieces constituting said adapter in order that their adjacent ends always face each other in every relative angular position of these two pieces. To ensure the coaxiality of the two strands of the light guide, a sleeve 73 is inserted with force fit into a bore 74 provided in the center of the bottom of bore 32 of piece 10. A tip 75 fixed at the end of strand 71 is provided with a bearing 76 set with force fit in a central bore 77 provided in the front face 45 of piece 9. Tip 75 is furthermore adjusted for an easy fit into the bore of sleeve 73. Strand 72 of the optic fiber similarly carries a tip 78 rigidly fixed to piece 10 and to sleeve 73. Packings 79 prevent infiltration of impurities in the space comprised between the ends of the two strands of the fiber optics.

Owing to the nature of the micromotor, piece 10 of the rotary adapter comprises, instead and at the place of the passage for cooling air of the motor in the preceding embodiments, a passage 80 for supplying the motor with compressed air and a passage 81 for the return of air to be evacuated from the motor. Whereas passage 81 brings the air to be evacuated from the motor back to the central chamber 82 between pieces 9, 10, wherefrom it can escape to the atmosphere through a passage (not shown) provided throughout piece 9, passage 80 communicating by means of a notch 83 provided in the wall of bore 32 with a groove 84 formed all around the bearing 22 of piece 9. A radial bore 85 sets that groove in communication with a passage 86 longitudinally bored in piece 9 and connected to a tube enclosed in sheath 7 and fed with compressed air to supply the motor. An additional packing 87 ensures the hermeticity of the annular space constituted by groove 84.

THE EMBODIMENT

Although an instrument equipped with fiber optics has been disclosed in detail only in combination with pneumatic motor, it should be quite clear that such a fiber also may be just as well arranged along the axis of rotation of the two pieces of the rotary adapter of the embodiments represented in FIGS. 2 to 5 comprising an electrical micromotor. The cooling air for such a motor need, indeed, not to be supplied through a central passage.

Since the coordinates and the sizes of the different passages and conduits of the dental instruments equipped with an air motor are standardized, it is possible to use the rotary adapter of the last embodiment with every existing instrument of the same type equipped with an air motor. It is, indeed, not indispensable that the handpiece comprise two nozzles for air and for water respectively. It may comprise only a single nozzle supplied with a cooling fluid produced by a mixer supplied with air and water and located already in the supply source or between the latter and the described instrument or in the intermediate section of the latter or in a piece inserted between this section and the handpiece or, finally, in tip means provided at the free end of a flexible tube of the handpiece, which extends on the outside of the latter, said tip means thereby being inserted in a lateral opening of the intermediate section. It is of course also possible to use any one of the rotary adapters disclosed hereinabove with an instrument arranged for receiving all handpieces in which the atomized jet supply is ensured either by an inner conduit or by an external flexible tube.

What is claimed is:

1. A dental instrument with a handpiece having a fore end and a rear end, comprising:
    at least one axially protruding portion located at the rear end of the handpiece;
    a tool carrying head being removably mounted at the fore end of the handpiece;
    an intermediate section having a fore end and a rear end, the intermediate section containing a micromotor for driving a tool carried by the head of the handpiece, the fore end of the intermediate section having complementary hole portions, equal in number to said at least one axially protruding portion, for receiving the axially protruding portions on the rear end of the handpiece, thereby non-rotatably fixing the rear end of the handpiece with the fore end of the intermediate section;
    a female portion of an adapter having a fore end and a rear end, the fore end of the female portion is fixed to the rear end of the intermediate section;
    a male portion of an adapter having a fore end and a rear end, the fore end of the male portion is rotatably mounted to the rear end of the female portion of the adapter; and
    a flexible sheath fixed to the rear end of the male portion of the adapter, the flexible sheath containing at least one supply source for the driving tool and the micromotor, the supply sources extending through said male and female portions.

2. The dental instrument of claim 1, wherein said at least one supply source comprises at least one supply line for at least one of electric current, compressed air, cooling air, water and fiber optics.

3. The dental instrument of claim 2, wherein the male and female portions of the adapter are rotatably mounted by an annular nut having an axially inner portion, the axially inner portion contacting at least one bearing located between the axially inner portion of the annular nut and a rear portion of the female portion of the adapter.

4. The dental instrument of claim 3, wherein said bearing comprises an annular array of bearings having an axially inner portion which contains a first annular ring located between the axially inner portion of the annular array of bearings and the rear portion of the female portion of the adapter.

5. The dental instrument of claim 4, wherein said at least one supply line for at least one of compressed air, cooling air, water and fiber optics extending through the male and female portions of the rotatable adapter, comprise at least one axially bored channel through the male and female portions, respectively, said at least one axially bored chamber in the male portion is communicated with an equal number of said at least one axially bored channel in the female portion, by an annular space therebetween.

6. The dental instrument of claim 5, wherein the annular spaces are sealed by sealing portions located on axially opposite sides of the annular space.

7. The dental instrument of claim 6, wherein the scaled annular space for the fiber optics supply means occurs entirely within the female portion of the adapter.

8. The dental instrument of claim 7, wherein the micromotor is supplied with electric current through the electric current supply source, the electric current supply source extending through the male and female portions of the adapter, comprising at least two axially bored channels through the male and female portions, respectively, the axially bored channels containing insulated current carrying wires therethrough, the current carrying wires being continuous from the flexible sheath portion to the micromotor.

9. The dental instrument of claim 8, wherein the male portion of the adapter cannot rotate a full 360° because of a stopping mechanism radially located between said male and female portions.

10. The dental instrument of claim 7, wherein the micromotor is supplied with electric current through the electric current supply source, the electric current source extending through the male and female portions of the adapter, comprising at least two axially bored channels through the male and female portions, respectively, the axially bored channels containing insulated current carrying wires therethrough, the current carrying wires in the male portion being electrically connected to current carrying wires in the female portion by an annular current carrying device located between said male portion and said female portion, the annular current carrying device providing electrical contact between current carrying wires in the male and female portions, respectively.

11. The dental instrument of claim 10, wherein the annular current carrying device comprises an insulating material having concentrically mounted current carrying annular rings mounted thereon, the concentrically mounted annular rings contacting axially biased brush members at a first portion and contacting electrical leads at a second portion.

12. The dental instrument of claim 1, wherein the micromotor is a fluid micromotor.

13. The dental instrument of claim 12, wherein said at least one supply source comprises supply lines containing the fluid and fiber optics.

14. The dental instrument of claim 13, wherein the male and female portions of the adapter are rotatably mounted by an annular nut having an axially inner portion, the axially inner portion contacting an annular array of bearings located between the axially inner portion of the annular nut and a rear portion of the female portion of the adapter, the supply lines comprise at least one axially bored channel through the male and female portions, respectively, said at least one axially bored channel in the male portion is communicated with said at least one axially bored channel in the female portion by an annular space therebetween.

15. The dental instrument of claim 14, wherein the annular spaces are sealed by sealing portions located on axially opposite sides of the annular space.

16. The dental instrument of claim 15, wherein the sealed annular space for the fiber optics supply means occurs entirely within the female portion of the adapter.

* * * * *